United States Patent [19]

Scott et al.

[11] Patent Number: 5,395,996
[45] Date of Patent: * Mar. 7, 1995

[54] CHEMICAL PROCESS

[75] Inventors: John D. Scott, Cheshire; Rachel A. Steven, Manley, both of England

[73] Assignee: Imperial Chemical Industries plc, London, United Kingdom

[*] Notice: The portion of the term of this patent subsequent to Sep. 7, 2010 has been disclaimed.

[21] Appl. No.: 11,537

[22] Filed: Feb. 1, 1993

Related U.S. Application Data

[63] Continuation of Ser. No. 804,550, Dec. 11, 1991, Pat. No. 5,243,105, which is a continuation of Ser. No. 676,703, Mar. 29, 1991, abandoned.

[30] Foreign Application Priority Data

Mar. 29, 1990 [GB] United Kingdom ............... 9007029

[51] Int. Cl.$^6$ .............................................. C07C 17/00
[52] U.S. Cl. .................................. 570/165; 570/166; 570/167; 570/168; 570/169
[58] Field of Search .............. 570/167, 168, 169, 165, 570/166

[56] References Cited

U.S. PATENT DOCUMENTS

| | | | |
|---|---|---|---|
| 2,005,710 | 6/1935 | Daudt. | |
| 2,637,747 | 5/1953 | McBee | 570/167 |
| 4,158,675 | 6/1979 | Putter | 570/169 |
| 4,605,798 | 8/1986 | Abel. | |
| 4,922,037 | 5/1990 | Manzer | 570/168 |
| 5,157,172 | 10/1992 | Wanzke et al. | 570/168 |

FOREIGN PATENT DOCUMENTS

| | | | |
|---|---|---|---|
| 0462514 | 12/1991 | European Pat. Off. | 570/167 |
| 2388785 | 12/1978 | France | 570/187 |

*Primary Examiner*—Alan Siegel
*Attorney, Agent, or Firm*—Cushman Darby & Cushman

[57] ABSTRACT 1,1,1,2-tetrafluoroethane (HFA 134a) is manufactured from trichloroethylene by a two-stage process comprising reacting trichloroethylene with hydrogen fluoride under superatmospheric pressure in a first reaction zone to form 1,1,1-trifluoro-2-chloroethane (133a) and reacting the 1,1,1-trifluoro-2-chloroethane with hydrogen fluoride in a second reaction zone to form 1,1,1,2-tetrafluoroethane; the entire product stream from the 133a reaction zone together with additional HF of required is fed through the 134a reaction zone. The two reaction zones may be provided within a single reaction vessel.

12 Claims, No Drawings

CHEMICAL PROCESS

This is a continuation of application Ser. No. 07/804,550, filed Dec. 11, 1991, now U.S. Pat. No. 5,243,105, which is a continuation of application Ser. No. 07/676,703, filed Mar. 29, 1991, now abandoned.

This invention relates to a chemical process and more particularly to a process for the manufacture of 1,1,1,2-tetrafluoroethane, known generally as HFA 134a.

Several methods have been proposed for the manufacture of 1,1,1,2-tetrafluoroethane (HFA 134a) which is useful as a replacement for CFCs in refrigeration and other applications. In United Kingdom Patent Specification No. 1,589,924 there is described the production of HFA 134a by the vapour phase fluorination of 1,1,1-trifluoro-2-chloroethane (HCFC 133a) which is itself obtainable by the fluorination of trichloroethylene as described in United Kingdom Patent Specification No. 1,307,224.

The formation of HFA 134a as a minor product of the fluorination of trichloroethylene is described in United Kingdom Patent Specification No. 819,849, the major reaction product being HCFC 133a. In WO 90/08755 there is described the conversion of trichloroethylene to HFA 134a wherein the two-stage reactions are carried out in a single reaction zone with recycle of part of the product stream.

Carrying out the conversion in a single reaction zone as described in WO 90/08755 suffers from the serious drawback that the fluorination catalyst tends to deactivate rapidly, largely as a result of carbon deposition and thus has a very short lifetime. For example we have found that operation of the single zone process using a chromia catalyst at 340° C. with a feed containing 10 molar % trichloroethylene and a contact time of 20 seconds resulted in fall in conversion of organics in the feed stream to HFA 134a to below 10% in a matter of less than 24 hours and that in order to maintain a conversion of 10% it was necessary to raise the temperature of the catalyst by some 30° to 40° C. (from 340° to 370°–380° C.) over a period of 4 days. This problem of short catalyst lifetime renders the single stage process unsuitable of practical adoption.

It has now been found that a two-step reaction sequence carried out in separate reaction zones as hereinafter described provides significantly improved yields of the desired product with high catalyst selectivity and high catalyst productivity and with an increased catalyst lifetime. For example, operation of the process of the invention under the conditions described above but with a 10 secs contact time in each reaction zone resulted in insignificant ageing of the catalyst over a period of 4 days; a rise in temperature by about 2° C. over the period of 4 days was sufficient to maintain a conversion of organics in excess of 10%.

It has been found that carrying out the two-step conversion of trichloroethylene to HFA 134a in separate reaction zones of equal size at atmospheric pressure in each reaction zone is impractical in that only low conversions of trichloroethylene, for example 20–30%, are obtained in the first reaction zone. The present invention enables trichlorethylene conversions of 90% or greater to be achieved.

According to the invention, there is provided a method for the manufacture of 1,1,1,2-tetrafluoroethane which comprises the steps of:

(A) contacting a mixture of trichloroethylene and hydrogen fluoride with a fluorination catalyst under super atmospheric pressure at a temperature in the range of about 200° to 400° C. in a first reaction zone to form a product containing 1,1,1-trifluoro-2-chloroethane and hydrogen chloride together with unreacted starting materials, (B) passing the total product of step A together with hydrogen fluoride to a second reaction zone containing a fluorination catalyst at a temperature in the range of about 280°–450° C. but higher than the temperature in step A to form a product containing 1,1,1,2-tetrafluoroethane, 1,1,1-trifluoro-2-chloroethane and hydrogen chloride, (C) treating the product of step B to separate 1,1,1,2-tetrafluoroethane and hydrogen chloride from 1,1,1-trifluoro-2-chloroethane and unreacted hydrogen fluoride, (D) feeding the 1,1,1-trifluoro-2-chloroethane mixture obtained from step C together with trichloroethylene and hydrogen fluoride to said first reaction zone (step A), and (E) recovering 1,1,1,2-tetrafluoroethane from the 1,1,1,2-tetrafluoroethane and hydrogen chloride separated out in step C.

The fluorination catalysts employed in steps A and B of the method of the invention may be the same or different (though preferably are the same) and may be supported or unsupported. Any of the fluorination catalysts described in the prior art may be used including various inorganic compounds, for example oxides, halides and oxyhalides of metals such as aluminium, cobalt, manganese, iron and especially chromium. Suitable chromium-containing catalysts include the oxide, hydroxide, oxyhalide, halides, inorganic acid salts, basic chromium fluoride and the catalysts described in United Kingdom Patent Specification No 1,307,224. Preferred catalysts are chromia and a zinc or nickel promoted chromia. Such catalysts may be Given a prefluorination treatment by passing hydrogen fluoride with or without nitrogen diluent over the catalyst at about 250°–450° C. to condition the catalyst prior to use.

The catalysts may be compressed into pellets and used in a fixed bed or, alternatively, catalysts of appropriate particle size may be used in a moving bed such as a fluidised bed.

A wide range of amounts of hydrogen fluoride may be employed in step B of the method of the invention, ranging from well below the stoichiometric amount to well above this amount. Typical amounts include from 1 to 10 moles, and preferably from 2 to 6 moles of hydrogen fluoride per mole of 1,1,1-trifluoro-2-chloroethane. Accordingly, the product of this reaction step will usually contain unreacted hydrogen fluoride in addition to 1,1,1,2-tetrafluoroethane, hydrogen chloride and by-products. Preferred reaction temperatures for this stage of the process are in the range from 285 to 385° C., especially 300° to 385° C. and more especially 325° to 385° C., with contact times of from 1 to 100 and preferably from 5 to 30 seconds at a pressure of 5 to 20 bars.

From 10 to 100, preferably from 15 to 60, moles of hydrogen fluoride per mole of trichloroethylene are typically employed in Step A. Again, the reaction product of this stage will normally contain unreacted hydrogen fluoride and perhaps low levels of unreacted trichloroethylene. Contact times of up to 100 seconds, preferably 5 to 30 seconds may be used, typically at 220°–350° C. and 5 to 20 bars pressure.

Step A is carried out under the superatmospheric pressure which is preferably at least 2 bars and more preferably at least 5 bars. In General, increasing the pressure results in an increase in catalyst productivity in step A. In practise the pressure will usually not exceed 30 bars. Step B may be carried out at atmospheric or superatmospheric pressure but in practice the pressure in step B will usually be the same as that in step A. In addition step C will usually be carried out at approximately the same pressure as steps A and B.

The reaction and separation steps which make up the method of the invention may be performed using conventional equipment and techniques. Thus, for example, recovery of 1,1,1,2-tetrafluoroethane in step E may be effected by washing the Gaseous tetrafluoroethane with water and aqueous sodium hydroxide solution and then drying and condensing the tetrafluoroethane.

It is preferred that the method of the invention is operated continuously. In practice, however, catalyst deactivation usually occurs requiring discontinuous operation of the process to permit catalyst regeneration or reactivation which may be conveniently effected by passing air or a mixture of air and inert Gas, for example nitrogen, over the catalyst at a temperature in the range of 300° to 500° C. A preferred catalyst reactivation process comprises heating the catalyst in a mixture of air and hydrogen fluoride, the resulting hot hydrogen fluoride being useable directly in step A and/or step B of the method according to the invention. The frequency of catalyst regeneration may be reduced if air is added to the reaction mixture in step A and step B of the process.

A particularly useful feature of the invention is that the exothermic conversion of trichloroethylene to 1,1,1-trifluoro-2-chloroethane in step A may be performed in a low cost adiabatic reactor, thereby providing significant cost advantages over reactor systems employing internal cooling surfaces. If desired, step B may also be carried out in an adiabatic reactor, using an interstage heater to raise the temperature of the gas stream between the two reactors.

The temperature employed in step A of the process is lower than the temperature employed in step B of the process. The recycle stream from step B may require cooling to or to below the temperature used in step A and a useful technique comprises mixing the trichloroethylene feed to step A with the recycle stream in advance of the step A reactor; in this way the recycle stream is cooled by the trichloroethylene whilst at the same time the trichloroethylene is heated, thereby reducing the need for external heating.

Separation of 1,1,1,2-tetrafluoroethane and hydrogen chloride from the product stream in step C of the process may be effected in any convenient manner, for example using a distillation technique.

As stated, the 1,1,1,2-tetrafluoroethane production process is carried out in two reaction zones operated at different temperatures. The two reaction zones may be provided in separate reactors if desired, but in a preferred feature of the invention the process is carried out in a single reactor containing both of the reaction zones. Thus, for example, the reactor may comprise a series of tubes through which the reactant steams are fed, each tube containing the fluorination catalyst and having a lower temperature length (for step A) and a higher temperature length for (step B). Trichloroethylene and hydrogen fluoride, together with a recycle stream (step D) are fed into the lower temperature end of the tube and a product stream containing 1,1,1,2-tetrafluoroethane is withdrawn from the higher temperature end of the tube. The reaction vessel may be an adiabatic reactor.

HFA 134a produced by the process of the invention contains a small amount, for example 200 to 1000 ppm, of the toxic impurity 1-chloro-2,2-difluoroethylene, commonly known as 1122. The procedure employed in the work-up of the product stream from step B (including the separation of step C) will usually contain one or more provisions for removing the 1122 which owing to its similar boiling point to HFA 134a tends to stay with the HFA 134a during the work-up operations.

At least part of the 1122 can be removed from the product stream prior to separation step C by contacting the product stream from step B together with hydrogen fluoride (already present in the product stream) over a fluorination catalyst such as chromia at a temperature in the range of about 150° to 250° C.

In the preferred embodiment of the invention described above in which step A and step B are carried out in different reaction zones of a single reactor, there may be provided a third reaction zone for treating the HFA 134a product stream with HF at a low temperature to remove at least part of the 1122 present in that product stream. Thus, for example, in the tube reactor described above, each tube containing a fluorination catalyst such as chromia may comprise a first zone maintained at a first temperature for carrying out step A, a second zone maintained at a higher temperature for carrying out step B and a third zone maintained at a lower temperature for carrying out 1122 removal from the product stream. Sufficient HF is fed with trichloroethylene (and the recycle stream) into the end of the tube to carry through to the second and third reaction zones.

Any 1122 present in the HFA 134a after step C can be removed by azeotropic distillation or extractive distillation and/or by contacting the HFA 134a with a zeolite molecular sieve.

The invention is illustrated but not limited by the following Example.

EXAMPLE 1

1,1,1,2-tetrafluoroethane was produced in a two-reactor system comprising a first reactor for converting trichloroethylene to 1,1,1-trifluoro-2-chloroethane (step A) and a second reactor for converting the 1,1,1-trifluoro-2-chloroethane from step A to 1,1,1,2-tetrafluoroethane (step B). Trichloroethylene and hydrogen fluoride were fed to the first, low temperature reactor (273° C.) at 13.5 bar. g. to convert the trichloroethylene selectively to 1,1,1-trifluoro-2-chloroethane (133a). The products of reactor 1 were then passed to a second, higher temperature, reactor operating at 366° C. and 13.5 bar. g. where the 133a produced in the first reactor was partially converted to HFA 134a. 133a was included in the feed to the 1st reactor together with the hydrogen fluoride and trichloro- ethylene to simulate a typical feed including recycle of 133a, HF and a small amount of trichloroethylene from the second reactor. Using an HF:Organics molar ratio of 3.5:1 at the first stage, and a 15% molar trichloroethylene content in the organics feed 133a to give a contact time of 13.5 seconds in each reactor, the reaction efficiencies for the two reactor system were measured and these are presented in Table 1.

For purposes of comparison, the above procedure was repeated using the same reactors but carrying out the reactions in both reactors at atmospheric pressure (contact time approximately 1 second). Reaction efficiencies are shown in Table 1. The results in Table 1 show the much improved catalyst productivity achieved by carrying out the reaction in the first reactor at superatmospheric pressure.

The process according to the invention was found to give significant catalyst productivity advantages as well as high reaction selectivity.

TABLE 1

| Reactor No. 1 | Reactor No. 2 | Trichloro-ethylene Conversion (%) | % Yields from trichloroethylene | | | R134a Selectivity (%) | R134a + R133a Selectivity (%) |
| --- | --- | --- | --- | --- | --- | --- | --- |
| | | | R133a | R134a | By-Products | | |
| Invention (super-atmospheric pressure) 273° C. (after 24 hrs) | 366° C. | 99.5 | 16.7 | 76.3 | 6.5 | 76.6 | 91.4 |
| Comparison (atmospheric pressure) 273° C. (after 24 hrs) | 366° C. | 97.0 | 59.8 | 26.2 | 11.0 | 27.01 | 88.7 |

We claim:

1. A method for the manufacture of 1,1,1,2-tetrafluoroethane which comprises the steps of:
    (A) contacting a mixture of trichloroethylene and hydrogen fluoride with a fluorination catalyst under superatmospheric pressure at a temperature in the range of about 200° to 400° C. in a first reaction zone to form a product containing 1,1,1-trifluoro-2-chloroethane and hydrogen chloride together with unreacted starting materials,
    (B) reacting the product of step (A) with hydrogen fluoride in a second reaction zone containing a fluorination catalyst at superatmospheric pressure and a temperature in the range of about 280°–450° C. but higher than the temperature in step (A) to form a product containing 1,1,1,2-tetrafluoroethane, 1,1,1-trifluoro-2-chloroethane and hydrogen chloride,
    (C) separating 1,1,1,2-tetrafluoroethane and hydrogen chloride from 1,1,1-trifluoro-1-chloroethane and unreacted hydrogen fluoride,
    (D) feeding the 1,1,1-trifluoro-2-chloroethane with trichloroethylene and hydrogen fluoride to said first reaction zone (step (A)), and
    (E) recovering the 1,1,1,2-tetrafluoroethane from the 1,1,1,2-tetrafluoroethane and hydrogen chloride separated out in step (C).

2. A method as claimed in claim 1, wherein 15 to 60 moles of hydrogen fluoride per mole of trichloroethylene are fed into the first reaction zone in step (A).

3. A method as claimed in claim 1 wherein the temperature in the first reaction zone in step A is in the range of from 220° C. to 350° C.

4. A method as claimed in claim 1 wherein 2 to 6 moles of hydrogen fluoride per mole of 1,1,1-trifluoro-2-chloroethane are fed into the second reaction zone in step (B).

5. A method as claimed in claim 1 wherein the temperature in the second reaction zone in step (B) is in the range of from 305° C. to 385° C.

6. A method as claimed in claim 1 wherein the contact time in step (A) and in step (B) is from 5 seconds to 30 seconds.

7. A method as claimed in claim 1 wherein the reactions in step (A) and step (B) are carried out at a pressure of from 5 bars to 20 bars.

8. A method as claimed in claim 1 which is operated continuously.

9. A method as claimed in claim 1 wherein said first and second reaction zones are provided by adiabatic reactors.

10. A method as claimed in claim 1 wherein the trichloroethylene fed into the first reaction zone in step (A) together with the product stream from step (B) is added to said product stream from step (B) in order to heat the trichloroethylene and cool the product stream in advance of the first reaction zone.

11. A method according to claim 1 1,1,1,2-tetrafluoroethane which comprises the steps of:
    (A) contacting a mixture of trichloroethylene and hydrogen fluoride with a fluorination catalyst under superatmospheric pressure at a temperature in the range of about 200° to 400° C. in a first reaction zone to form a product containing 1,1,1-trifluoro-2-chloroethane and hydrogen chloride together with unreacted starting materials,
    (B) reacting the product of step (A) with hydrogen fluoride in a second reaction zone containing a fluorination catalyst at superatmospheric pressure and a temperature in the range of about 280°–450° C. but higher than the temperature in step (A) to form a product containing 1,1,1,2-tetrafluoroethane, 1,1,1-trifluoro-2-chloroethane and hydrogen chloride, and
    (C) recovering the 1,1,1,2-tetrafluoroethane, said including an additional reaction zone wherein reaction product containing 1,1,1,2-tetrafluoroethane is treated at a lower temperature to remove at least part of any 1-chloro-2,2-difluoroethylene which may also be present in the reaction product.

12. The method of claim 11 wherein the treatment in the additional reaction zone comprises contacting the reaction product with hydrogen fluoride over a fluorination catalyst at a temperature of about 150° to 250° C.

* * * * *